United States Patent
Tkachenko et al.

(10) Patent No.: US 11,969,702 B2
(45) Date of Patent: Apr. 30, 2024

(54) SEALED MICROWELL ASSAY

(71) Applicants: Celldom, Inc., San Carlos, CA (US); The Regents of the University of California, Oakland, CA (US)

(72) Inventors: Natalia Tkachenko, San Diego, CA (US); Eugene Tkachenko, Del Mar, CA (US); Alexander Groisman, San Diego, CA (US); Edgar Gutierrez, Spring Valley, CA (US)

(73) Assignees: Celldom, Inc., San Carlos, CA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 15/927,057

(22) Filed: Mar. 20, 2018

(65) Prior Publication Data
US 2018/0280918 A1    Oct. 4, 2018

Related U.S. Application Data

(60) Provisional application No. 62/474,283, filed on Mar. 21, 2017.

(51) Int. Cl.
*B01J 19/00* (2006.01)
*B01L 3/00* (2006.01)
(Continued)

(52) U.S. Cl.
CPC ......... *B01J 19/0046* (2013.01); *B01L 3/5085* (2013.01); *C12N 15/1013* (2013.01);
(Continued)

(58) Field of Classification Search
CPC ............ B01J 19/0046; B01L 3/5085; C12N 15/1013; C12Q 1/02; C40B 40/06; G01N 33/5005; G01N 33/54366
(Continued)

(56) References Cited

U.S. PATENT DOCUMENTS 6,027,695 A    2/2000  Oldenburg
6,083,761 A *  7/2000  Kedar ............... B01L 3/5025
                                                 436/178
(Continued)

FOREIGN PATENT DOCUMENTS

GB    2524541    *  3/2014
GB    2524541    *  9/2015
(Continued)

OTHER PUBLICATIONS

Kaya et al.; Respiration activity of *Escherichia coli* entrapped in a cone-shaped microwell and cylindrical micropore monitored by scanning electrochemical microscopy (SECM); Analyst. Jun. 2004;129(6):529-34; Abstract.

Šeila Selimovic et al.; Microfabricated polyester conical microwells for cell culture applications; Lab Chip. Jul. 21, 2011; 11(14): 2325-2332.
(Continued)

*Primary Examiner* — Benjamin R Whatley
*Assistant Examiner* — Jacqueline Brazin
(74) *Attorney, Agent, or Firm* — TMB Law; Timothy M. Brown

(57) ABSTRACT

The present invention provides methods, systems and kits for performing microwell analysis in sealed small volumes. The microwells of the invention are sealed through the pairing of microwell and bead geometry wherein the diameter of the beads is greater than the diameter of the bottom of the microwells. Loading the beads into the microwells seals samples within an analytical space between the bottom of a nested bead and the bottom of the subject microwell.

27 Claims, 9 Drawing Sheets

(51) Int. Cl.
*C12N 15/10* (2006.01)
*C12Q 1/02* (2006.01)
*C40B 40/06* (2006.01)
*G01N 33/50* (2006.01)
*G01N 33/543* (2006.01)

(52) U.S. Cl.
CPC ............. *C12Q 1/02* (2013.01); *C40B 40/06* (2013.01); *G01N 33/5005* (2013.01); *G01N 33/54366* (2013.01); *B01J 2219/00317* (2013.01); *B01J 2219/005* (2013.01); *B01J 2219/00648* (2013.01); *B01L 2300/0829* (2013.01); *B01L 2300/0851* (2013.01); *B01L 2300/0858* (2013.01)

(58) Field of Classification Search
USPC ..................................................... 422/430
See application file for complete search history.

(56) References Cited

U.S. PATENT DOCUMENTS

| | | | |
|---|---|---|---|
| 6,171,780 B1 * | 1/2001 | Pham | B01L 3/5085 422/552 |
| 7,351,592 B2 | 4/2008 | Storek | |
| 7,431,887 B2 | 10/2008 | Storek | |
| 7,651,868 B2 | 1/2010 | McDevitt | |
| 7,998,746 B2 * | 8/2011 | Otillar | B01L 3/502738 436/151 |
| 8,257,967 B2 | 9/2012 | McDevitt | |
| 8,859,204 B2 | 10/2014 | Brown | |
| 9,611,507 B2 | 4/2017 | Seul | |
| 2002/0160363 A1 | 10/2002 | McDevitt | |
| 2002/0197622 A1 | 12/2002 | McDevitt | |
| 2003/0012693 A1 * | 1/2003 | Otillar | G01N 27/745 506/39 |
| 2003/0032002 A1 | 2/2003 | Wang et al. | |
| 2003/0064422 A1 | 4/2003 | McDevitt | |
| 2003/0124029 A1 | 7/2003 | Webb et al. | |
| 2003/0170883 A1 | 9/2003 | Martin et al. | |
| 2004/0063100 A1 | 1/2004 | Wang | |
| 2004/0053322 A1 | 3/2004 | McDevitt | |
| 2004/0159798 A1 | 8/2004 | Martin et al. | |
| 2005/0112277 A1 * | 5/2005 | Banerjee | B01J 19/0046 427/372.2 |
| 2006/0013736 A1 | 1/2006 | Blok et al. | |
| 2006/0019264 A1 | 1/2006 | Attiya | |
| 2006/0228740 A1 * | 10/2006 | Seul | B01J 19/0046 435/287.2 |
| 2008/0014631 A1 * | 1/2008 | Muraguchi | G01N 33/54366 435/288.7 |
| 2008/0095673 A1 | 4/2008 | Xu | |
| 2009/0010388 A1 | 1/2009 | Stahly et al. | |
| 2010/0028935 A1 | 2/2010 | Ciaiolo et al. | |
| 2011/0046008 A1 * | 2/2011 | Love | B82Y 30/00 506/9 |
| 2011/0086778 A1 | 4/2011 | Herrmann et al. | |
| 2011/0136677 A1 * | 6/2011 | Oldham | B01L 3/502715 427/256 |
| 2011/0195496 A1 | 8/2011 | Muraguchi et al. | |
| 2011/0244448 A1 | 10/2011 | Shirai | |
| 2011/0294678 A1 | 12/2011 | Jin et al. | |
| 2012/0135396 A1 | 5/2012 | McDevitt | |
| 2012/0202709 A1 * | 8/2012 | Bergo | C40B 30/10 506/12 |
| 2012/0276541 A1 | 11/2012 | Lian et al. | |
| 2013/0260410 A1 | 10/2013 | Johansen et al. | |
| 2014/0287402 A1 | 4/2014 | Garrone et al. | |
| 2014/0155295 A1 | 6/2014 | Hindson et al. | |
| 2014/0323330 A1 * | 10/2014 | Bergo | G01N 33/54373 506/9 |
| 2015/0017709 A1 | 1/2015 | Brown | |
| 2015/0141261 A1 | 5/2015 | Hunicke-Smith et al. | |
| 2015/0238956 A1 | 8/2015 | Grouzmann et al. | |
| 2016/0144360 A1 | 5/2016 | Lacey et al. | |
| 2016/0145683 A1 | 5/2016 | Fan et al. | |
| 2016/0257993 A1 | 9/2016 | Fu et al. | |
| 2016/0265069 A1 | 9/2016 | Fan et al. | |
| 2016/0289669 A1 | 10/2016 | Fan et al. | |
| 2017/0242020 A1 | 8/2017 | Yamauchi | |
| 2017/0307502 A1 * | 10/2017 | Mason | G01N 15/1459 |

FOREIGN PATENT DOCUMENTS

| | | | |
|---|---|---|---|
| JP | 2016-533187 A1 | 10/2016 | |
| JP | 2017049151 | 3/2017 | |
| JP | 2017049151 A1 | 3/2017 | |
| WO | 2000014540 A1 | 3/2000 | |
| WO | 2002025289 A1 | 3/2002 | |
| WO | WO-2014072432 A1 * | 5/2014 | ............ C12M 21/08 |
| WO | 2014-176435 | 10/2014 | |
| WO | 2014/176435 A2 † | 10/2014 | |
| WO | 2014176435 A1 | 10/2014 | |
| WO | 2015-031691 A1 | 3/2015 | |
| WO | WO-2015031691 A1 * | 3/2015 | ............ C12Q 1/6874 |
| WO | 2015/145280 A1 † | 10/2015 | |
| WO | 2016/118915 A1 † | 7/2016 | |

OTHER PUBLICATIONS

Fan et al.; Combinatorial labeling of single cells for gene expression cytometry; Science. 2015 Feb. 2015; vol. 347, Issue 6222: 1258367. 1-1258367.8.

Macosko et al.; Highly Parallel Genome-wide Expression Profiling of Individual Cells Using Nanoliter Droplets; Cell 161, 1202-1214, May 21, 2015.

Huang et al; Centrifugation-assisted single-cell trapping (CAScT) in a truncated cone-shaped microwell array (TCMA) chip for the . . . ; DOI: 10.1021/acs.analchem.5b03031.

Bose et al.; Scalable microfluidics for single-cell RNA printing and sequencing; Genome Biology (2015) 16:120.

Yuan et al; An Automated Microwell Platform for Large-Scale Single Cell RNA-Seq; http://dx.doi.org/10.1101/070193.

Reproducible and Uniform Embryoid Bodies Using AggreWell™ Plates; Stem Cell Technologies; Technical Manual; www.stemcell.com.

Microgrid arrays; www.microsurfaces.com.au/microgrid.html.

Micromesh arrays; www.microsurfaces.com.au/micromesh.html.

Gierahn et al.; Seq-Well: A Portable, Low-Cost Platform for High-Throughput Single-Cell RNA-Seq of Low-Input Samples; Apr. 2017 ; 14(4): 395-398.

Extended European Search Report for EP Application No. 18771335.9 (EPO child application of U.S. Appl. No. 15/927,057).

Non-Final Office Action in Co-pending U.S. Appl. No. 16/178,488 dated Mar. 16, 2021.

Office Action for related Japan Patent Application No. 2020-501416 dated Mar. 8, 2022.

Final Office Action for Copending U.S. Appl. No. 16/178,448 dated Oct. 21, 2021.

Non-Final Office Action for Copending U.S. Appl. No. 16/178,448 dated Mar. 2, 2022.

Office Action for co-pending China patent application No. 2018800338207 dated Feb. 28, 2023.

* cited by examiner
† cited by third party

SEALED MICROWELL ASSAY

CROSS-REFERENCE TO RELATED APPLICATIONS

This application claims priority to Provisional Application No. 62/474,283 filed Mar. 21, 2017, the entire contents of which are incorporated herein by reference for all purposes.

FIELD OF THE INVENTION

The invention relates to assays for microwell analysis. More particularly, the invention relates to providing sealed microwell assays for the analysis of biological samples in small volumes.

BACKGROUND

Microwell arrays for biological assays have been in use for some time. One of the applications for microwell arrays is the determination of the expression profiles for single cells. For example, U.S. Patent Application Publication No. 2016/0289669 by Fan et al. discloses microwell-based devices and systems for single cell expression profile analysis wherein single cells and single ligand-coated beads are loaded into a microwell and permitted sediment to the bottom of the microwell prior to conducting an analysis on the biological activity of the cells. However, the microwells remain in an unsealed state while the analysis is performed.

The device and systems of Fan et al. produce a number of deficiencies. First, the unsealed state of the microwells permits the uncontrolled exchange of targeted biomolecules between microwells resulting in microwell cross-contamination and compromised accuracy of the single cell analysis. As shown by Yuan and Sims (Scientific Reports 6, Article number: 33883 (2016)), this problem can be mitigated by covering microwells with a layer of oil which is immiscible in water, but the assay becomes more complicated as a result. A microwell-based assay described in a recent publication (Gierahn et al., Nat Methods. 2017 April; 14(4): 395-398) attempts to provide a sealed microwell configuration through the use of a semipermeable membrane. However, this approach also complicates microwell analysis by requiring additional steps in the application of its microwell technology. Second, in a microwell configuration where a bead and a cell are placed next to each other, the volume of the medium into which the content of the cell is released is relatively large compared to the volume of the cell, resulting in substantial dilution of the released biomolecules and, hence, reduced binding efficiency to the ligands on the bead. This limitation is also inherent to the semipermeable membrane-based approach to the sealing of microwells. Third, it is difficult to pair exactly one bead to one cell in a microwell configuration when the bead and the cell are placed next to each other on the bottom of a microwell. Fourth, the distance between the bead and cell usually varies among microwells in the array, resulting in additional microwell-to-microwell variability in the binding efficiency between targeted biomolecules and the beads. Thus, there exists a need for improving the accuracy, ease of use, and efficiency of contemporary microwell-based assays, including microwell-based assays for single cell analysis.

SUMMARY OF THE INVENTION

The invention provides systems, methods, devices and kits for enhancing the accuracy and efficiency of microwell-based assays. The invention enhances the accuracy and efficiency of microwell analysis by enclosing samples within small volumes in microwells through a novel geometric pairing of microwells and beads. This geometric pairing provides a number of advantages. First, enclosing the sample prevents the cross-contamination of materials between neighboring microwells. Second, enclosing the sample through the geometric pairing of microwells and beads enables a reduction of the effective volume of medium carrying the sample, thus increasing the concentration of the sample and hence, the ligand binding efficiency. Third, the geometric pairing of microwells and beads only allows one bead to enter a microwell, thus preventing a situation when a cell in a microwell is paired with more than one bead. Finally, the position of the beads with respect to cells in the microwells remains highly consistent.

DETAILED DESCRIPTION

The invention relates to improving the efficiency and accuracy of microwell analysis. More particularly, the invention relates to systems, methods, devices and kits for improving the efficiency and accuracy of microwell analysis.

Existing microwell systems suffer serious limitations in terms of their ability to efficiently and accurately analyze samples in individual microwells within an array. These limitations result, in part, from the lack of a means for enclosing samples within individual microwells within an array. The lack of a sealing functionality permits targeted analytes to diffuse or flow from one well to another, leading to cross-contamination which compromises the analysis of samples. This shortcoming can be particularly problematic in the context of performing single cell expression profile analysis, such as in the systems and methods disclosed in U.S. Patent Application Publication No. 2016/0289669 to Fan et al. Fortunately, the inventor recognized that these limitations in microwell analysis can be overcome through a novel combination of microwell and bead geometry that permits samples to be effectively sealed within a small analytical space.

The inventor surprisingly discovered that a sealed analytical space within a microwell can be formed by pairing the geometry of the microwell with the geometry of a bead such that the surface of the bead contacts the walls of the microwell thereby forming a seal at the microwell-bead interface. The sealed analytical space provides a number of advantages over contemporary microwell analysis. Sealing of the analytical space prevents, or at least inhibits, the egress and ingress of targeted analytes from and to individual microwells, thereby improving assay accuracy by preventing cross-contamination of neighboring microwells within an array. In some embodiments, the geometric pairing of microwells and beads can allow only one bead to enter a microwell, thus preventing a situation when a cell in a microwell is paired with more than one bead.

Figure 1:
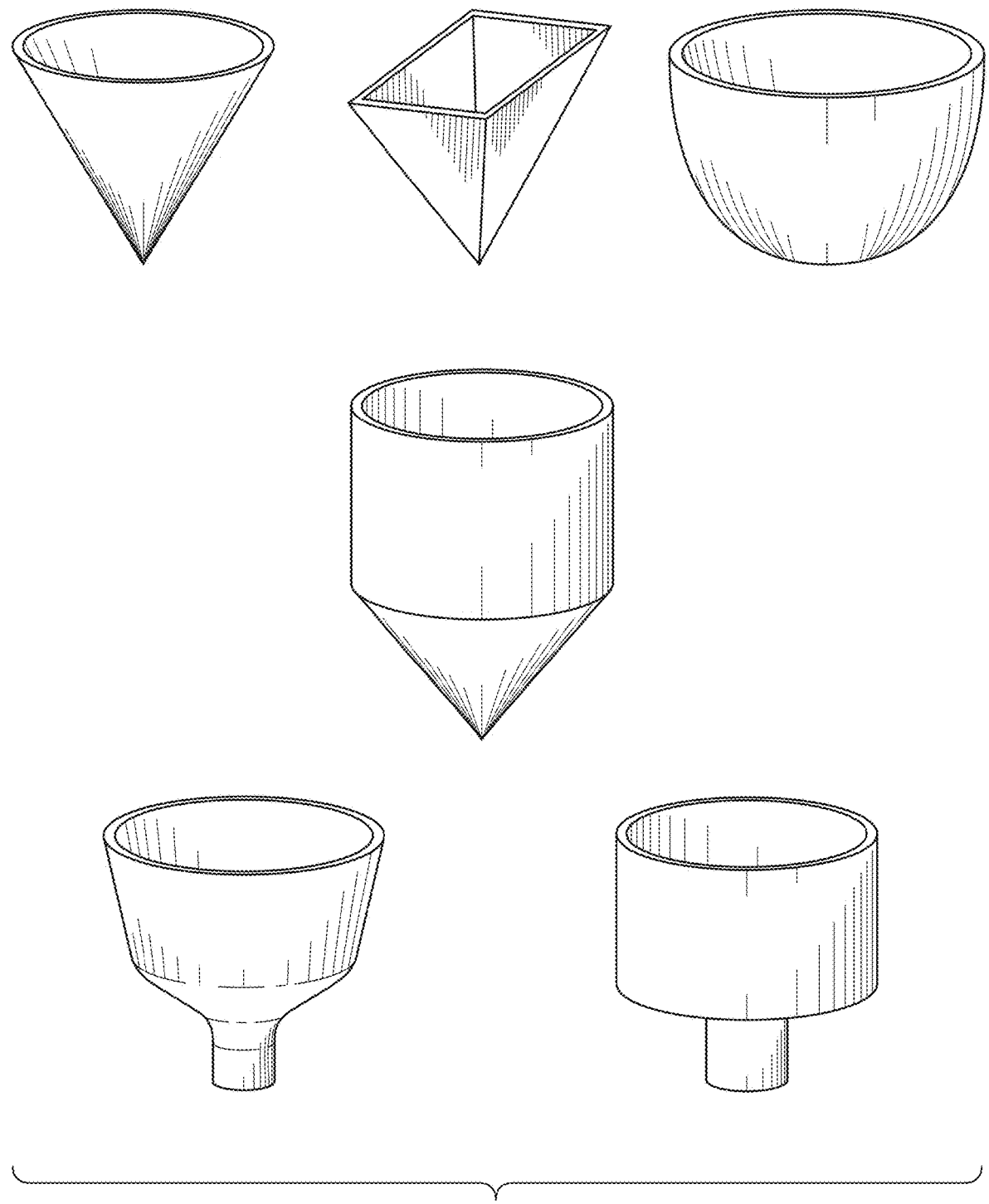
FIG. 1 shows a perspective view of some non-limiting embodiments of the microwells of the invention.
Figure 2:
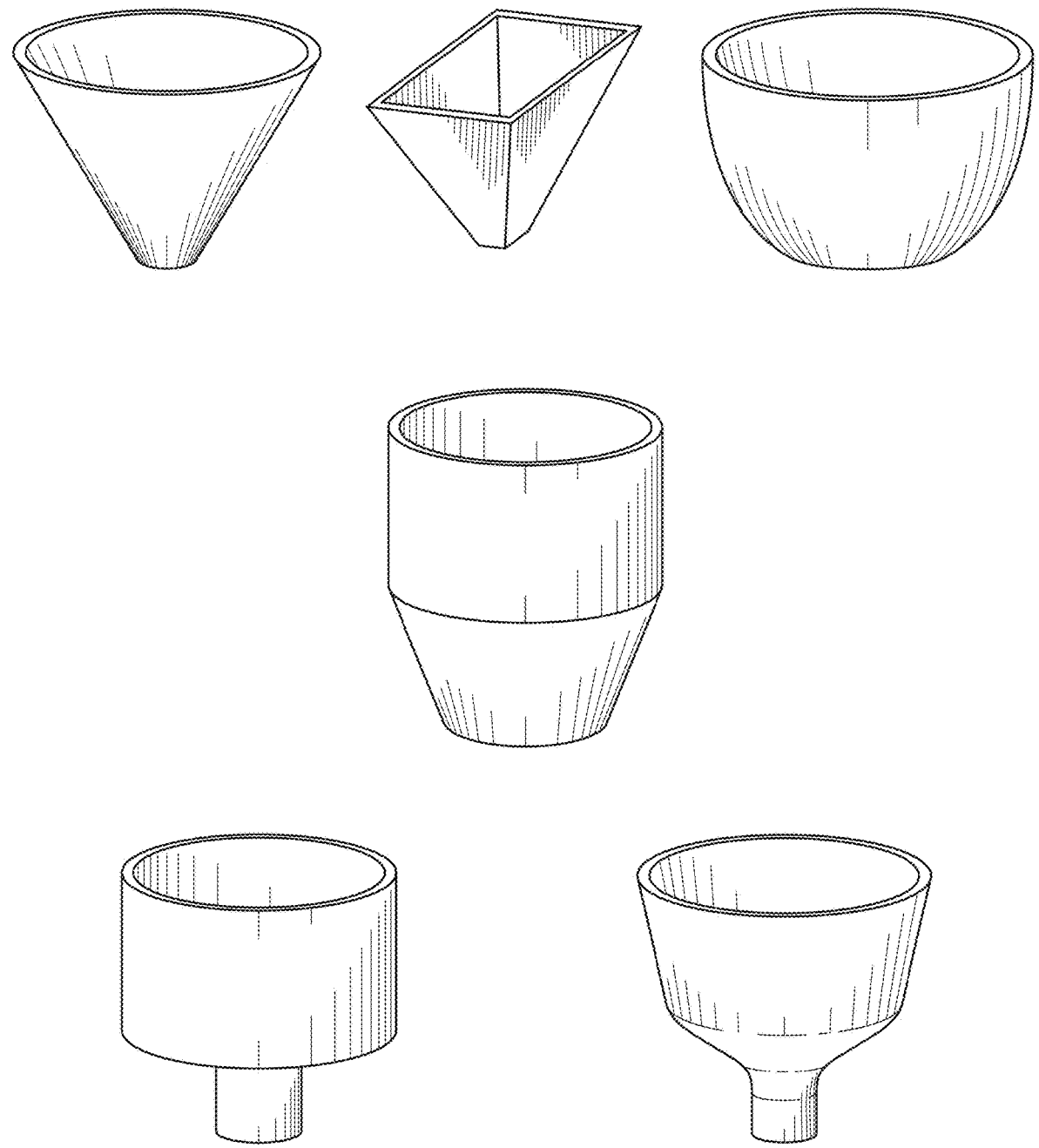
FIG. 2 shows a perspective view of some non-limiting embodiments of the frustum-shaped microwells of invention.
Figure 3:
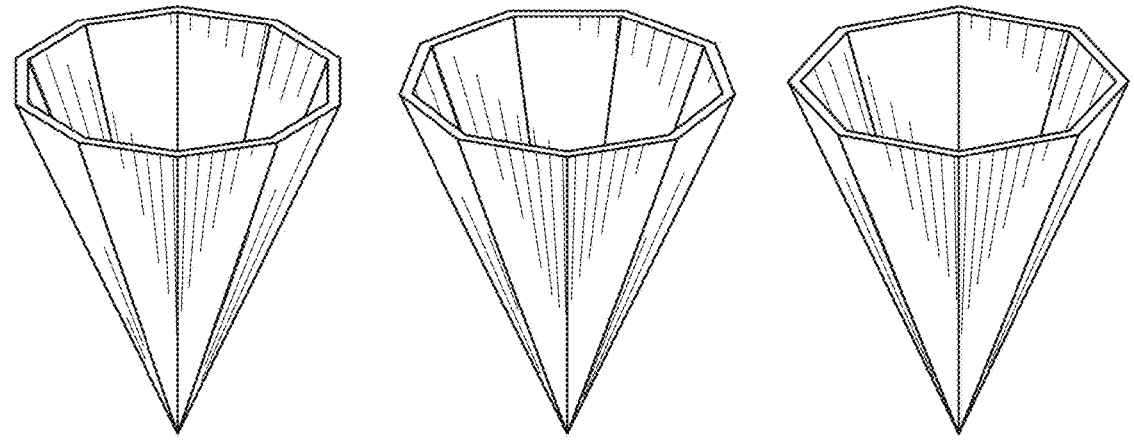
FIG. 3 shows a perspective view of some non-limiting embodiments the polygonal-shaped microwells of the invention.
Figure 3:
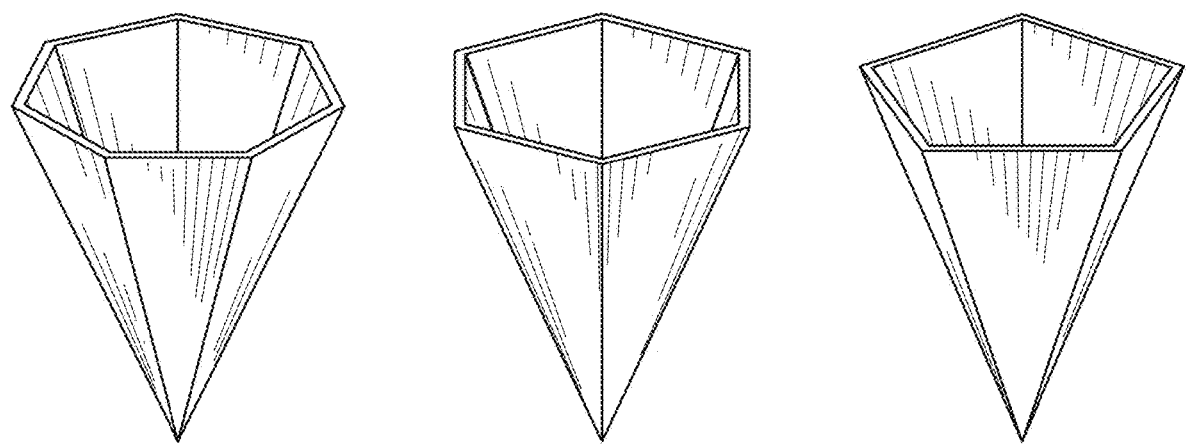
Figure 4:
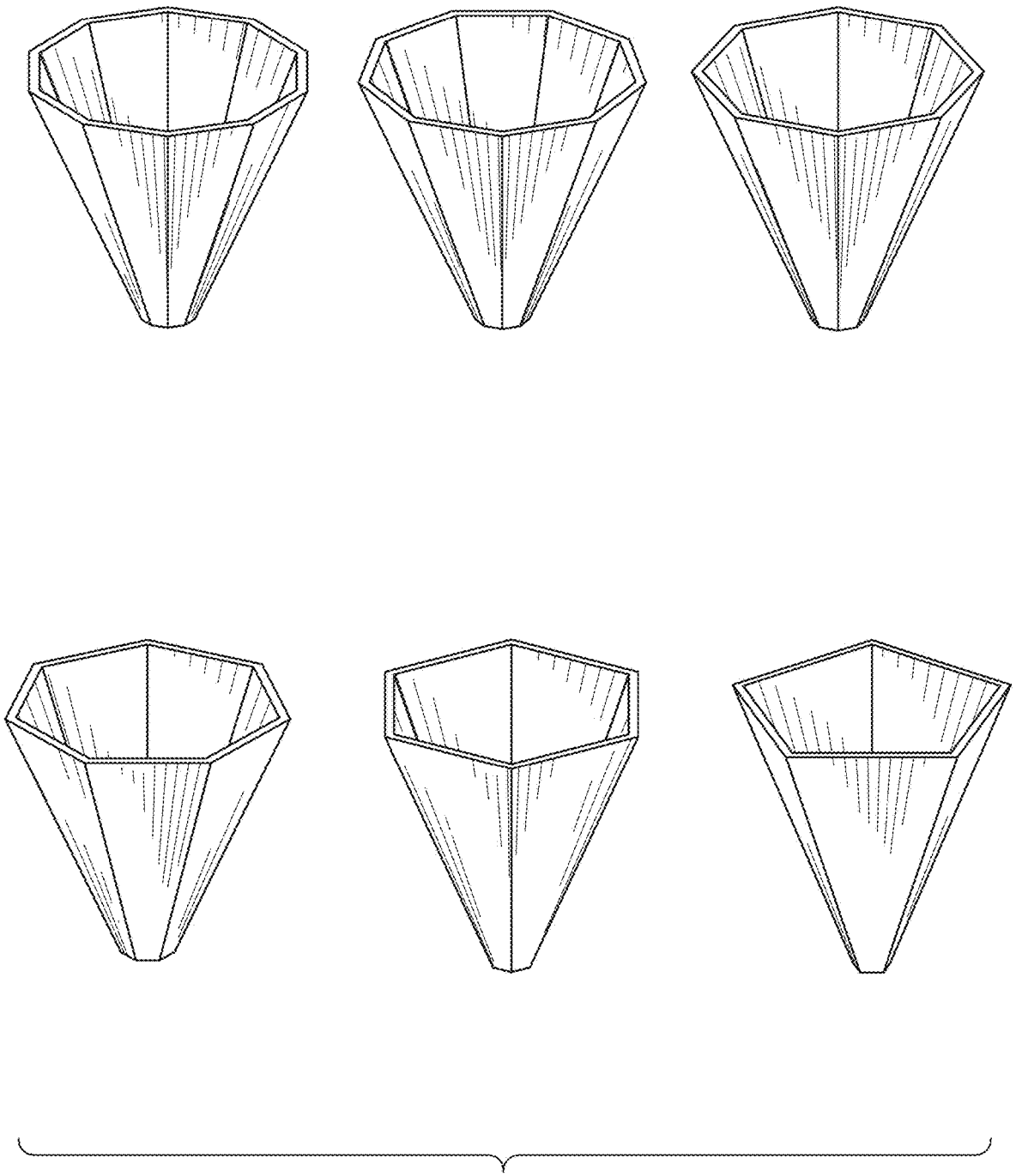
FIG. 4 shows a perspective view of some non-limiting embodiments of the frustum-shaped polygonal microwells of the invention.

In at least some embodiments of the invention, a sealed analytical space is achieved by pairing the geometry of the microwell and the geometry of the bead such that the width of the bead is greater than the width of the bottom of the microwell. Accordingly, microwells for use with the invention can assume any geometric shape wherein the top (i.e. opening) of the microwell has a width that is greater than the width of the bottom of the microwell. Suitable geometric shapes for the microwells, include, but are not limited to, cylinders, polyhedrons, inverted cones, inverted pyramids, hemispheres, or combinations thereof. Suitable shapes for the microwells include, but are not limited to, those depicted in FIG. 1. The microwells can be in the shape of a frustum. The microwells can assume a frustum having the shape of an inverted pyramid, a cylinder, a polyhedron, an inverted cone, a hemisphere, or combinations thereof. Suitable frustum shapes for the microwells include, but are not limited to, those depicted in FIG. 2. The microwells can be in the shape of an inverted cone. The microwells can be in the shape of an inverted truncated cone. The microwells can be in the shape of a cylinder that terminates in a cone. The microwells can be in the shape of a cylinder that terminates in a truncated cone. The microwells can be in the shape of a cylinder that terminates in an inverted pyramid. The microwells can be in the shape of a cylinder that terminates in a truncated, inverted pyramid. The microwell can be in the shape of a cylinder that terminates in a smaller cylinder having a closed bottom. The microwell can be in the shape of a cylinder that terminates in a hemisphere having a smaller diameter than the cylinder. The top of the microwell, and conjoining sides, can have a transverse cross-section that is circular, elliptical or polygonal. The top of the microwell, and conjoining sides, can have a transverse cross-section that is a triangle, quadrilateral, pentagon, hexagon, heptagon, octagon, nonagon, or decagon. Suitable microwells having a polygonal transverse cross-section, include, but are not limited to, those depicted in FIGS. 3 and 4.

Figure 5:
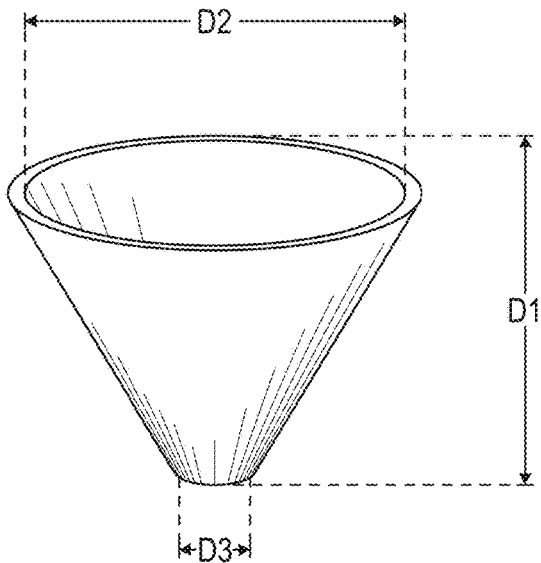
FIG. 5 shows the dimensions of a non-limiting embodiment of a microwell of the invention.

At least one aspect of the invention concerns the dimensions of the microwells. A non-limiting description of the relative dimensions of the microwells is depicted in FIG. 5. The microwells can have a depth D1 which spans from the top of the microwell to the bottom inner surface of the microwell. Depth D1 can be between about 5 µm and about 300 µm. As used herein, the term "about" can refer the stated value with which the term is combined, or a value that varies (plus or minus) up to 30%, up to 25%, up to 20%, up to 15%, up to 10%, up to 9%, up to 8%, up to 7%, up to 6%, up to 5%, up to 4%, up to 3%, up to 2% or up to 1% the stated value. Depth D1 can be at least at least 5 µm, at least 10 µm, at least 15 µm, at least 20 µm, at least 25 µm, at least 30 µm, at least 35 µm, at least 40 µm, at least 45 µm, at least 50 µm, at least 60 µm, at least 70 µm, at least 80 µm, at least 90 µm, at least 100 µm, at least 110 µm, at least 120 µm, at least 130 µm, at least 140 µm, at least 150 µm, at least 160 µm, at least 170 µm, at least 180 µm, at least 190 µm, at least 200 µm, at least 210 µm, at least 220 µm, at least 230 µm, at least 240 µm, at least 250 µm, at least 260 µm, at least 270 µm, at least 280 µm, at least 290 µm, or at least 300 µm. Depth D1 can be up to 5 µm, up to 10 µm, up to 15 µm, up to 20 µm, up to 25 µm, up to 30 µm, up to 35 µm, up to 40 µm, up to 45 µm, up to 50 µm, up to 60 µm, up to 70 µm, up to 80 µm, up to 90 µm, up to 100 µm, up to 110 µm, up to 120 µm, up to 130 µm, up to 140 µm, up to 150 µm, up to 160 µm, up to 170 µm, up to 180 µm, up to 190 µm, up to 200 µm, up to 210 µm, up to 220 µm, up to 230 µm, up to 240 µm, up to 250 µm, up to 260 µm, up to 270 µm, up to 280 µm, up to 290 µm, or up to 300 µm.

In some preferred embodiments, the width of the top (i.e. opening) of the microwells is proportionately greater than the width of the bottom of the microwells. Referring to FIG. 5, the top of the microwell can have a width (i.e. diameter) D2 of between about 30 µm to 200 µm. The bottom of the microwell can have a width (e.g. diameter) D3 of about 5 µm and 50 µm. Width D2 can be at least 30 µm, at least 35 µm, at least 40 µm, at least 45 µm, at least 50 µm, at least 55 µm, at least 60 µm, at least 65 µm, at least 70 µm, at least 75 µm, at least 80 µm, at least 85 µm, at least 90 µm, at least 95 µm, at least 100 µm, at least 110 µm, at least 120 µm, at least 130 µm, at least 140 µm, at least 150 µm, at least 160 µm, at least 170 µm, at least 180 µm, at least 190 µm, at least 200 µm, at least 210 µm, at least 220 µm, at least 230 µm, at least 240 µm, at least 250 µm, at least 260 µm, at least 270 µm, at least 280 µm, at least 290 µm, at least 300 µm, or at least a width that intervenes one of these specifically referenced widths. Width D2 can be up to 30 µm, up to 35 µm, up to 40 µm, up to 45 µm, up to 50 µm, up to 55 µm, up to 60 µm, up to 65 µm, up to 70 µm, up to 75 µm, up to 80 µm, up to 85 µm, up to 90 µm, up to 95 µm, up to 100 µm, up to 110 µm, up to 120 µm, up to 130 µm, up to 140 µm, up to 150 µm, up to 160 µm, up to 170 µm, up to 180 µm, up to 190 µm, up to 200 µm, up to 210 µm, up to 220 µm, up to 230 µm, up to 240 µm, up to 250 µm, up to 260 µm, up to 270 µm, up to 280 µm, up to 290 µm, up to 300 µm, or up to a width that intervenes one of these specifically referenced widths. Width D3 can be at least 5 µm, at least 6 µm, at least 7 µm, at least 8 µm, at least 9 µm, at least 10 µm, at least 11 µm, at least 12 µm, at least 13 µm, at least 14 µm, at least 15 µm, at least 16 µm, at least 17 µm, at least 18 µm, at least 19 µm, at least 20 µm, at least 21 µm, at least 22 µm, at least 23 µm, at least 24 µm, at least 25 µm, at least 26 µm, at least 27 µm, at least 28 µm, at least 29 µm, at least 30 µm, 35 µm, at least 40 µm, at least 45 µm, at least 50 µm, or at least a width that intervenes one of these specifically referenced widths. Width D3 can be up to 5 µm, up to 6 µm, up to 7 µm, up to 8 µm, up to 9 µm, up to 10 µm, up to 11 µm, up to 12 µm, up to 13 µm, up to 14 µm, up to 15 µm, up to 16 µm, up to 17 µm, up to 18 µm, up to 19 µm, up to 20 µm, up to 21 µm, up to 22 µm, up to 23 µm, up to 24 µm, up to 25 µm, up to 26 µm, up to 27 µm, up to 28 µm, up to 29 µm, up to 30 µm, up to 35 µm, up to 40 µm, up to 45 µm, up to 50 µm, or up to a width that intervenes one of these specifically referenced widths. In some preferred embodiments, width D3 is 15 µm. The ratio of width D3 at the bottom of the microwell to width D2 at the top of the microwell can be between about 0.99 to 0.05. The ratio of width D3 to width D2 can be up to 0.99, up to 0.95, up to 0.90, up to 0.85, up to 0.80, up to 0.75, up to 0.70, up to 0.65, up to 0.60, up to 0.55, up to 0.50, up to 0.45, up to 0.40, up to 0.35, up to 0.30, up to 0.25, up to 0.20, up to 0.15, up to 0.10, up to 0.05, or up to any ratio that intervenes these specifically listed ratios. Width D2 at the top of the microwell may range from about 1-fold to about 10-fold of the width D3 at the bottom of the microwell. Width D2 can be at least 1-fold, at least 1.5-fold, at least 2-fold, at least 3-fold, at least 4-fold, at least 5-fold, or at least 10-fold the width of D3.

While a conical frustum is depicted in FIG. 5, one skilled in the art will appreciate that the invention can be practiced with any geometrical shape wherein the width at the top of the microwell is proportionately greater than the width at the bottom of the microwell. Microwells for use with the invention can have any volume that permits the microwells to be used for their intended purpose. The microwells can have a volume ranging from about 0.1 picoliter to about 100,000 picoliters. In some embodiments, each microwell has a volume of about 144 picoliters.

In some embodiments, the walls of the microwells may be slanted wherein a positive draft angle gives rise to a larger opening at the top of the well. In some embodiments, the walls may be slanted positively or negatively by at least 1 degree, at least 2 degrees, at least 3 degrees, at least 4 degrees, at least 5 degrees, at least 6 degrees, at least 7 degrees, at least 8 degrees, at least 9 degrees, at least 10 degrees, at least 11 degrees, at least 12 degrees, at least 13 degrees, at least 14 degrees, or at least 15 or more degrees. In some embodiments, the walls may be slanted positively or negatively by at most 1 degree, at most 2 degrees, at most 3 degrees, at most 4 degrees, at most 5 degrees, at most 6 degrees, at most 7 degrees, at most 8 degrees, at most 9 degrees, at most 10 degrees, at most 11 degrees, at most 12 degrees, at most 13 degrees, at most 15 degrees, or at most 15 or more degrees. In these embodiments, therefore, the top of the microwell can have a different diameter (or average diameter) than the bottom of the microwells. In some preferred embodiments, the walls are slanted by a positive draft angle in the range of about 10 to about 30 degrees. In some embodiments, the opening angle of the microwells is two times greater than the average draft angle. The opening angle of the microwells can be between about 0° and about 60°. The opening angle can be up to 60°, up to 55°, up to 50°, up to 45°, up to 40°, up to 35°, up to 30°, up to 25°, up to 20°, up to 15°, up to 10°, up to 5°, up to 1°, or up to any opening angle that intervenes these specifically listed angles. The opening angle can be up to about 10°, about 11°, about 12°, about 13°, about 14°, about 15°, about 16°, about 17°, about 18°, about 19°, about 20°, about 21°, about 22°, about 23°, about 24°, about 25°, about 26°, about 27°, about 28°, about 29°, about 30°, about 31°, about 32°, about 33°, about 34°, about 35°, about 36°, about 37°, about 38°, about 39°, about 40°, about 41°, about 42°, about 43°, about 44°, about 45°, about 46°, about 47°, about 48°, about 49°, about 50°, about 51°, about 52°, about 53°, about 54°, about 55°, about 56°, about 57°, about 58°, about 59°, or about 60°. In some preferred embodiments, the opening angle is 34° or 35°.

At least one aspect of the invention concerns the geometry of the beads that are paired with the microwells. The beads can be spherical or substantially spherical. The beads can be microspheres. The beads can have a width (i.e. diameter) that is between about 10 µm and about 100 µm. The beads width can be at least 10 µm, at least 15 µm, at least 20 µm, at least 25 µm, at least 30 µm, at least 35 µm, at least 40 µm, at least 45 µm, at least 50 µm, at least 55 µm, at least 60 µm, at least 65 µm, at least 70 µm, at least 75 µm, at least 80 µm, at least 85 µm, at least 90 µm, at least 95 µm, at least 100 µm, or at least a width that intervenes these specific widths. The beads can have a width up to 10 µm, up to 15 µm, up to 20 µm, up to 25 µm, up to 30 µm, up to 35 µm, up to 40 µm, up to 45 µm, up to 50 µm, up to 55 µm, up to 60 µm, up to 65 µm, up to 70 µm, up to 75 µm, up to 80 µm, up to 85 µm, up to 90 µm, up to 95 µm, up to 100 µm, or up to a width that intervenes these specific widths. For the geometric pairing of the microwell with the bead, the ratio of the width of the bottom of the microwell to the width of the bead can be any ratio wherein the width of the bead is proportionately greater than the width of the bottom of the microwell. The ratio of the width of the bottom of the microwell to the width of the bead can range from about 0.05 to about 0.99. In some embodiments, the ratio of the width of the bottom of the microwell to the width of the bead is at most 0.99, at most 0.95, at most 0.9, at most 0.8, at most 0.7, at most 0.6, at most 0.5, at most 0.4, at most 0.3, at most 0.2, at most 0.1, or at most 0.05. One skilled in the art will appreciate that the ratio can be any ratio that intervenes those listed here, such as 0.37. One skilled in the art will further appreciate that the bead widths referenced herein can refer to a mean bead diameter in instances where a plurality of beads are contemplated.

Beads for use with the invention can be fabricated from a material selected from the group consisting of polymethylmethacrylate, epoxy, silicon, fused-silica, glass, a polymer, a metal, alumina, an elastomer, polydimethylsiloxane, agarose, and a hydrogel, or any combination thereof. Examples of beads suitable for use with the invention include, but are not limited to, streptavidin conjugated beads, agarose beads, magnetic beads, glass beads, Dynabeads®, MACS® microbeads, antibody conjugated beads (e.g., anti-immunoglobulin microbead), protein A conjugated beads, protein G conjugated beads, protein A/G conjugated beads, protein L conjugated beads, oligo-dT conjugated beads, silica beads, silica-like beads, anti-biotin microbeads, and BcMag™ Carboxy-Terminated Magnetic Beads. The beads can be polymethylmethacrylate microspheres. The beads can have a density of between about 1 g/cm$^3$ and about 4 g/cm$^3$. The beads can have a density of up to 2 g/cm$^3$, up to 3 g/cm$^3$, up to 4 g/cm$^3$, or up to any density that intervenes the specifically listed densities. The beads can have a density of at least 1 g/cm³, at least 2 g/cm³, at least 3 g/cm³, at least 4 g/cm³, or at least any density that intervenes these specifically listed densities. The beads can be associated with (e.g. impregnated with) quantum dots or fluorescent dyes to make them fluorescent in one fluorescence optical channel or multiple optical channels. The beads can be magnetic. The beads can be associated with iron oxide or chromium oxide to make them paramagnetic or ferromagnetic. The beads can be functionalized. When used in reference to a bead, the terms "functionalized", "functional" and the like, refer to a bead having at least one ligand on its surface for capturing a targeted analyte. The ligand can be an antibody, peptide, protein, an oligonucleotide, or combinations thereof. The beads can be non-spherical in shape, such as an elliptical shape having an elliptical longitudinal cross-section and a circular transverse cross-section.

Figure 6:
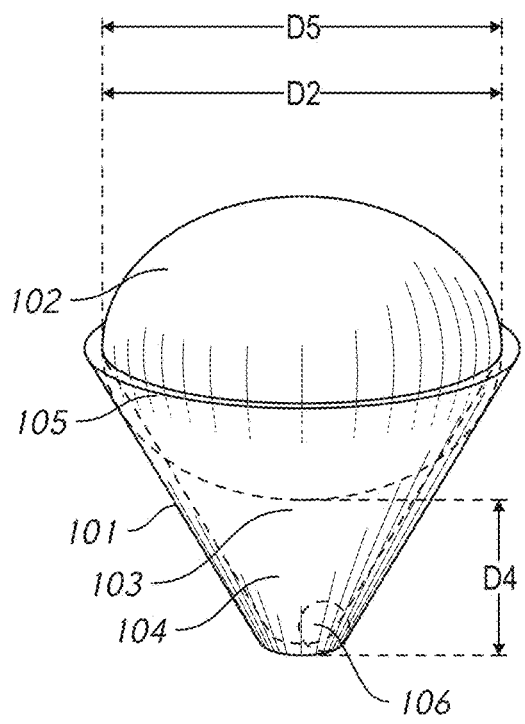
FIG. 6 shows a perspective view of a non-limiting embodiment of a geometric pairing of a microwell and a bead.

FIG. 6 shows a non-limiting embodiment of a pairing of microwell and bead geometry wherein microwell 101 is in contact with bead 102, such that the bottom of bead 102 is at distance D4 from the bottom of microwell 101. In the embodiment shown in FIG. 6, bead 102 has width D5 which is the same as, or approximately the same as, width D2 at the opening of microwell 101 such that bead 102 contacts the top of microwell 101 around the perimeter of bead 102 to form interface 105. With bead 102 in contact with microwell 101 around interface 105, the bottom of bead 102 rests above the bottom of the microwell at distance D4. With bead 102 in contact with microwell 101, analytical space 104 is formed in the area between interface 105 and the bottom of microwell 101. Interface 105 can prevent, or at least inhibit, the ingress and egress of an analyte from analytical space 104.

While a particular pairing of a bead and microwell geometry is shown in FIG. 6, one skilled in the art will appreciate that other geometric pairings are possible, provided that the width of the bead is greater than the width of the bottom of the microwell. For example, it may be desirable to provide deeper nesting of the bead within the microwell in order to create a smaller volume in the analytical space, to bring the bead within closer proximity to a sample within the analytical space, and/or provide greater anchoring strength of the bead within the microwell. Accordingly, the geometric pairing of the bead and microwell may be such that the bead has a width that is greater than the bottom of the microwell, but less than the width of the opening of the microwell. One non-limiting example of such an embodiment is depicted in FIG. 7.

Figure 7:
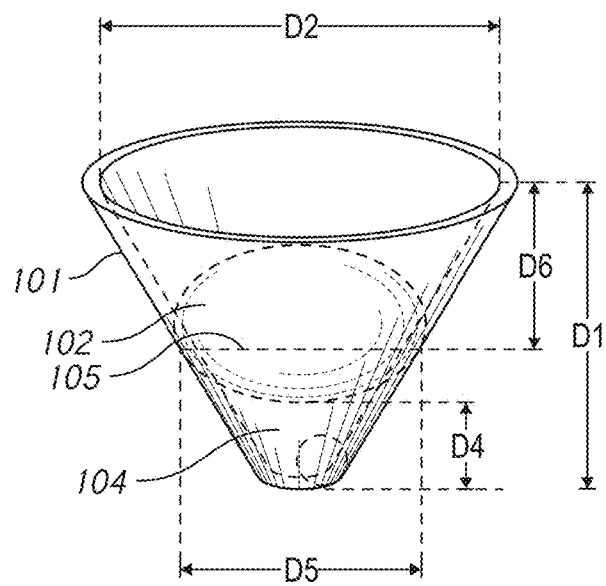
FIG. 7 shows a perspective view of a non-limiting embodiment of a geometric pairing of a microwell and a bead.

As shown in FIG. 7, bead 102 can have width D5 which is less than width D2 at the top (i.e. opening) of microwell 101, but still greater than the width of the bottom of the microwell. Due to the width of bead D5 being less than the width of the opening of microwell D2, bead 102 contacts the walls of microwell 101 at interface 105 at distance D6 from the top of microwell 101. Contact of bead 102 with the wall of microwell 101 at interface 105 forms analytical space 104 within the area between interface 105 and the bottom microwell 101. As interface 105 is formed at distance D6 from the top of microwell 101, analytical space 104 has a smaller relative volume than embodiments where the bead forms an interface at the top of the microwell such as, for example, the embodiment depicted in FIG. 6. In a non-limiting embodiment of the invention, microwell 101 assumes a frustum in the shape of an inverted cone, wherein depth D1 is about 50 µm, width D2 at the top of the microwell is about 50 µm, width D3 at the bottom of the microwell is about 15 µm, the bead width D5 is about 30 µm, and the volume of analytical space 104 is about 2 pL to about 4 pL. In another non-limiting embodiment of the invention, microwell 101 assumes a frustum in the shape of an inverted cone, wherein depth D1 is about 75 µm, width D2 at the top of the microwell is about 50 µm, width D3 at the bottom of the microwell is about 15 µm, and the bead width D5 is about 30 µm.

It will be appreciated by one skilled in the art that the geometric pairing of the microwell and the bead can be adjusted to achieve a desired distance between the bottom of the microwell and the bottom of a bead that is nested within the microwell. For example, the skilled artisan may desire to adjust the distance between the bottom of the microwell and the bottom of the nested bead based on the average diameter of a cell to be analyzed so as to bring ligands on the surface of a functionalized bead into a close proximity to the cell. Similarly, the skilled artisan may desire to decrease the volume of the analytical space to increase the concentration of an analyte within the reaction mixture. Referring to FIGS. 6 and 7, the geometric pairing of microwell 101 and bead 102 can be designed to achieve a desired distance between the bottom of bead 102 and the upper surface of cell 106 contained within analytical space 104 and resting on the bottom of microwell 101. The distance between the bottom of bead 102 and cell 106 can be between about 1 m and about 30 µm. The distance between the bottom of bead 102 and cell 106 can be at least 1 m, at least 2 µm, at least 3 µm, at least 4 µm, at least 5 µm, at least 10 µm, at least 15 µm, at least 20 µm, at least 25 µm, or at least 30 µm. The geometric pairing of the microwell and bead can similarly be chosen to achieve a desired volume for the space between the bottom of the bead and the bottom of the microwell. Still referring to FIGS. 6 and 7, the geometric pairing of microwell 101 and bead 102 can be chosen to provide an analytical space 104 having a volume of between about 0.1 to about 100 pL. The geometric pairing of microwell 101 and bead 102 can be chosen to provide an analytical space 104 having a volume of at least 0.1 pL, at least 0.5 pL, at least 1 pL, at least 5 pL, at least 10 pL, at least 15 pL, at least 20 pL, at least 30 pL, at least 40 pL, at least 50 pL, at least 60 pL, at least 70 pL, at least 80 pL, at least 90 pL, at least 100 pL, or at least any volume that intervenes these specifically listed volumes. The geometric pairing of microwell 101 and bead 102 can be chosen to provide an analytical space 104 having a volume of up to 0.1 pL, up to 0.5 pL, up to 1 pL, up to 5 pL, up to 10 pL, up to 15 pL, up to 20 pL, up to 30 pL, up to 40 pL, up to 50 pL, up to 60 pL, up to 70 pL, up to 80 pL, up to 90 pL, up to 100 pL, or up to any volume that intervenes these specifically listed volumes.

Referring to FIGS. 6 and 7, distance D4 can be adjusted by varying the geometric pairing of microwell 101 and bead 102 such that distance D4 comprises between 0.05% and 99% of the microwell's depth D1. Distance D4 can be at least 99%, at least 90%, at least 85%, at least 80%, at least 75%, at least 70%, at least 65%, at least 60%, at least 55%, at least 50%, at least 45%, at least 40%, at least 35%, at least 30%, at least 25%, at least 20%, at least 15%, at least 10%, at least 9%, at least 8%, at least 7%, at least 6%, at least 5%, at least 4%, at least 3%, at least 2%, at least 1%, at least 0.5%, at least 0.25%, at least 0.2%, at least 0.15%, at least 0.10%, or at least 0.5% of depth D1. Distance D4 can be up to 99%, up to 90%, up to 85%, up to 80%, up to 75%, up to 70%, up to 65%, up to 60%, up to 55%, up to 50%, up to 45%, up to 40%, up to 35%, up to 30%, up to 25%, up to 20%, up to 15%, up to 10%, up to 9%, up to 8%, up to 7%, up to 6%, up to 5%, up to 4%, up to 3%, up to 2%, up to 1%, up to 0.5%, up to 0.25%, up to 0.2%, up to 0.15%, up to 0.10%, or up to 0.5% of depth D1.

The geometric pairing of the microwell and bead can be designed to provide contact between the bead and microwell at a desired periphery of the bead surface. The periphery can be the periphery (i.e. outer surface) of a spherical bead. The geometric pairing can result in contact between the microwell walls and the periphery of the bead, wherein the width (e.g. diameter) of the bead periphery in contact with the walls of the microwell is equal to, or less than, the width (e.g. diameter) of the bead. It will be understood that the periphery of the bead in contact with the walls of the microwell equates to the circumference of the bead in the horizontal plane where the bead contacts the walls of the microwell. The ratio between the width of the bead and the width of the bead periphery in contact with the walls of the microwell can be up to 1.0, up to 0.9, up to 0.8, up to 0.7, up to 0.6, up to 0.5, up to 0.4, up to 0.3, up to 0.2, up to 0.1, or up to any ratio that intervenes these specifically listed ratios. The geometric pairing of the microwell and the bead can result in contact between the periphery of the bead and the walls of the microwell at the top (i.e. opening) of the microwell. The geometric pairing of the microwell and bead can result in contact between the periphery of the bead and the walls of the microwell below the top of the microwell. The geometric pairing can result in contact between the periphery of the bead and the walls of the microwell, wherein at least a portion of the bead protrudes above the top of the microwell. The height of the portion of the bead that protrudes above the top of the microwell can be greater than, equal to, or less than, the radius of the bead. The ratio between the height of the portion of the bead that protrudes above the top of the microwell and the radius of the bead can be up to 2.0, up to 1.9, up to 1.8, up to 1.7, up to 1.6, up to 1.5, up to 1.4, up to 1.3, up to 1.2, up to 1.1, up to 1.0, up to 0.9, up to 0.8, up to 0.7, up to 0.6, up to 0.5, up to 0.4, up to 0.3, up to 0.2, up to 0.1, or up to any ratio that intervenes these specifically listed ratios. The portion of the bead that protrudes above the top of the microwell can be up to 100% of the volume of the bead, up to 90% of the volume of the bead, up to 80% of the volume of the bead, up to 70% of the volume of the bead, up to 60% of the volume of the bead, up to 50% of the volume of the bead, up to 40% of the volume of the bead, up to 30% of the volume of the bead, up to 20% of the volume of the bead, up to 10% of the volume of the bead, up to 5% of the volume of the bead, up to 1% of the volume of the bead, or any percentage volume that intervenes these specifically listed percentages. The geometric pairing of the bead and microwell can result in contact between the periphery of the bead and the walls of the microwell, wherein the top of the bead lies below the plane that defines the top of the microwell.

Figure 8A:
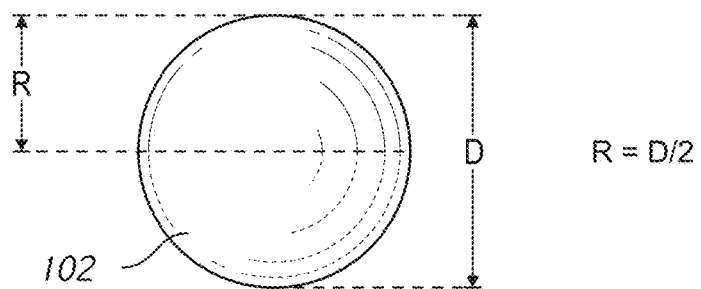
FIG. 8A shows the relative dimensions of a bead.
Figure 8B:
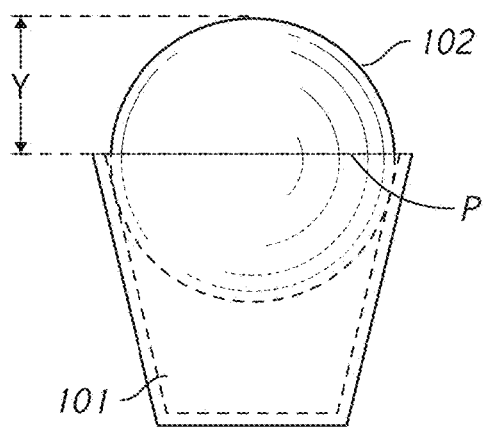
FIG. 8B shows an embodiment of geometric pairing between a bead and a microwell wherein the height of the portion of the bead that lies above the top of the microwell is equal to the radius of the bead.
Figure 8C:
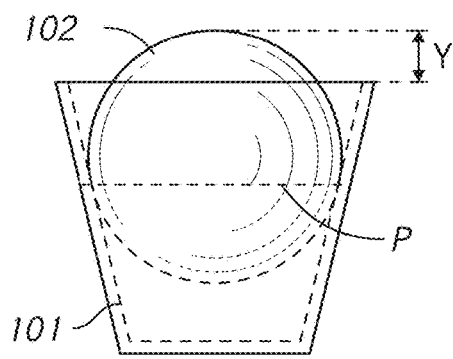
FIG. 8C shows an embodiment of the geometric pairing between a bead and a microwell wherein the height of the portion of the bead that lies above the top the microwell is less than the radius of the bead.
Figure 8D:
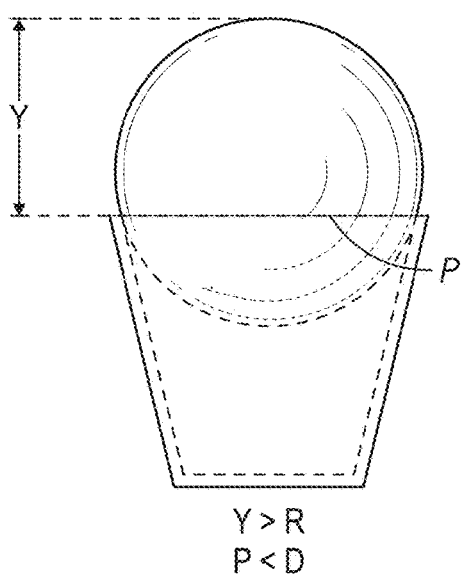
FIG. 8D shows an embodiment of the geometric pairing between a bead and a microwell wherein the height of the portion of the bead that lies above the top the microwell is greater than the radius of the bead.

Some non-limiting embodiments for the geometric pairing of the microwell and bead are shown in FIGS. 8B through 8D. FIG. 8A shows the relative dimensions of a bead having diameter D and radius R. FIG. 8B depicts a geometric pairing of microwell 101 and bead 102, wherein the height Y of the portion of the bead that protrudes above the top (i.e. top horizontal plane) of microwell 101 is equal to radius R. FIG. 8C depicts a geometric pairing of microwell 101 and bead 102, wherein the height Y of the portion that protrudes above the top of microwell 101 is less than radius R. Referring to FIG. 8C, the ratio between the height Y and radius R can be up to 1.0, up to 0.9, up to 0.8, up to 0.7, up to 0.6, up to 0.5, up to 0.4, up to 0.3, up to 0.2, up to 0.1, or up to any ratio that intervenes these specifically listed ratios. FIG. 8D depicts a geometric pairing of microwell 101 and bead 102, wherein the height Y of the portion that protrudes above the top of microwell 101 is greater than radius R. Referring to FIG. 8D, the ratio between height Y and radius R can be up to 2.0, up to 1.9, up to 1.8, up to 1.7, up to 1.6, up to 1.5, up to 1.4, up to 1.3, up to 1.2, up to 1.1, or up to any ratio that intervenes these specifically listed ratios.

FIGS. 8B through 8D further show a non-limiting aspect of the invention wherein the geometric pairing of the bead and the microwell can be designed to achieve physical contact between the walls of the microwell and a desired periphery between the middle of the bead and the bottom of the bead. As shown in FIG. 8B, bead 102 contacts microwell 101 at interface P, wherein the width of interface P (i.e. the distance spanning opposite sides of the bead that are in contact with the walls of the microwell) is equal to diameter D of bead 102. Though not depicted, one skilled in the art will appreciate that FIGS. 8B through 8D show a side view of the geometric pairing of a microwell and a bead, and that interface P is formed along the periphery (i.e. circumference) of bead 102 where it contacts with the walls of microwell 101. FIGS. 8C and 8D show embodiments wherein the width of interface P is less than diameter D of bead 102. The width of interface P can be equal to, or less than, diameter D of bead 102. The ratio of the width of interface P to diameter D can be up to 1.0, up to 0.9, up to 0.8, up to 0.7, up to 0.6, up to 0.5, up to 0.4, up to 0.3, up to 0.2, up to 0.1, or up to any ratio that intervenes these specifically listed ratios. In one preferred embodiment, the ratio of the width of interface P to diameter D can be up to 1.0, up to 0.9, up to 0.8, up to 0.7, up to 0.6, up to 0.5, up to 0.4, up to 0.3, up to 0.2, up to 0.1, or up to any ratio that intervenes these specifically listed ratios, wherein (i) no portion Y protrudes above the top of microwell 101, or (ii) the height of portion Y is less than radius R. Such configurations may be desirable to: achieve greater nesting of the bead within the microwell so as to resist dislodging of the bead from the microwell due to Brownian movement and/or the convective flow of a fluid over the top of the microwell; achieve a smaller volume for the analytical space that is defined by the region between the surface of the bottom half of the bead, starting from interface P and down, and the bottom of microwell 101; and/or bring the bottom of bead 102 into closer proximity with a sample (e.g. cell) at the bottom of microwell 101.

In some embodiments, the geometrical pairing between the bead and the microwell is such that a microwell can only accommodate a single bead. This single bead to microwell functionality can be achieved in embodiments wherein the top of an anchored bead protrudes above the top (i.e. opening) of the microwell such as depicted in FIGS. 6, 8B, 8C, and 8D (i.e. with a positive protrusion wherein Y>0). Such configurations can prevent the entry of a second bead into the microwell. The single bead to microwell functionality can also be achieved in embodiments where no portion of a nested bead protrudes above the opening of the microwell, such as depicted in FIG. 7, when the distance between the top of the microwell and the top of the bead is sufficiently small. In such embodiments, a single bead is anchored within the microwell at a depth such that while a second bead may enter or rest in the microwell, this second bead can easily be dislodged such as by a gentle convective flow. The single bead to microwell configuration can benefit single cell expression analysis as it prevents a single cell from interacting with multiple beads which gives the false impression that ligands bound to the beads are derived from more than one cell.

In at least some embodiments of the invention, a plurality of microwells as disclosed herein are formed within a substrate to provide a microwell array. In some embodiments, the substrate comprises from 100 to 100,000,000 microwells. In some embodiments, the substrate comprises from 100 to 50,000,000 microwells. In some embodiments, the substrate comprises up to 100,000,000 microwells. In some embodiments, the substrate comprises up to 50,000,000 microwells. In some embodiments, the substrate comprises from 10,000 to 200,000 microwells. The substrate can be fabricated from a material selected from the group consisting of silicon, fused-silica, glass, a polymer, a metal, an elastomer, polydimethylsiloxane, agarose, and a hydrogel, or any combination thereof. One skilled in the art will appreciate that when a plurality of the microwells disclosed herein are incorporated into a substrate to form a microwell array, the dimensions of the microwells described herein can refer to the average or mean dimensions of such plurality of microwells.

The present invention provides methods for analyzing the bioactivity in a sample, and methods for identifying the presence of an analyte in a sample. The methods can be practiced by providing a substrate comprising at least one microwell, loading a sample into the microwell, and loading at least one bead onto the substrate. The geometry of the microwell and bead can be paired such that loading the bead onto the substrate results in the bead nesting within the microwell and contacting the walls of the microwell to form an interface that encloses the sample within a space between the bead and the bottom of the microwell. The substrate can be an array of microwells as disclosed herein. The microwells can be one or more of the microwells disclosed herein. The beads can be the beads disclosed herein.

In at least one embodiment, the invention provides a method for analyzing the bioactivity of a sample. Analyzing the bioactivity of a sample can comprise detecting the presence or absence of one or more analytes in the sample. Analyzing the bioactivity of the sample can comprise determining the amount of one or more analytes in the sample. The analyte can be a biomolecule, wherein analyzing the activity of the sample comprises identifying the presence or absence of one or more biomolecules in the sample. The analyte can be a biomolecule, wherein analyzing the activity of the sample comprises determining the amount of one or more biomolecules in the sample. The terms "product" and "analyte" are used interchangeably herein to refer to a substance that is of interest (i.e. targeted) for analysis. The analyte can be a biomolecule. As used herein, the term "biomolecule" includes, but is not limited to, proteins, polypeptides, oligopeptides, peptides, polynucleotides, oligonucleotides, nucleotides, nucleic acids (e.g., including DNA (such as cDNA and genomic DNA) and RNA (such as mRNA and tRNA)), polysaccharides, oligosaccharides, lipids, antibody (e.g. heavy and light polypeptide chain antibody), cell receptors, low weight molecules (e.g., hormones, ligands, signal transduction substances, low-weight organic molecules, etc.), and complex molecules thereof, and the like. In some embodiments, the biomolecule is mRNA. In some embodiments, determining the bioactivity of a sample comprises determining the number of copies of at least one oligonucleotide in the sample. In some embodiments, determining the bioactivity of a sample comprises determining the number of copies of at least one oligonucleotide in the sample, wherein the sample is a cell. In some embodiments, the analyte can be a cell, virus, organelle, or part of a tissue. In some embodiments, the analyte can be a plurality of cells, a plurality of viruses, a plurality of organelles, or plurality of tissue specimens.

The beads can be loaded onto the substrate (i.e. microwell array) as a suspension with the beads suspended in a liquid carrier. The beads can have a greater density than the liquid carrier so that individual beads settle into individual microwells when the suspension is loaded onto the microwell array. The number of beads loaded onto the substrate can be proportionately greater than, equal to, or proportionately less than, the number of microwells in the array. The number of beads loaded onto the microwell array can be smaller than the number of microwells to limit the number of beads that are not anchored inside microwells. The number of beads loaded onto the substrate can be greater than the number of microwells in the substrate to minimize the number of microwells having no beads anchored within them. The beads can be loaded onto the substrate in a bead-to-microwell ratio of 1:1, 1.1:1, 1.2:1, 1.3:1, 1.4:1 or 1.5:1. As noted herein, the geometric pairing of the bead and microwell can facilitate the loading of single beads within individual microwells in an array. In embodiments wherein at least a portion of an anchored bead protrudes above the top of the microwell, the portion of the bead protruding above the microwell can prevent other beads from entering the microwell. In embodiments wherein the upper surface of the bead lies below the plane of the top of the microwell, a second bead can rest on top of the bead that is already anchored in the microwell. Nevertheless, the forces holding this second bead can be sufficiently weak so that only minimal agitation, such as originating from convective flow, is required to remove the second bead from its position on top of the anchored bead without dislodging the anchored bead.

The sample can be a cell or a plurality of cells. The sample can be a plurality of clonal cells, or a plurality of mixed cells. Suitable samples for analysis by the disclosed methods, systems and kits of the invention include any sample comprising a plurality of cells, such as, for example, cell cultures, blood samples, tissue samples in which the extracellular matrix has been digested or dissolved to release individual cells into suspension, and the like. The plurality of cells may be derived from a single sample, or from two or more samples that have been combined, and may comprise a plurality of cells of the same type, or a plurality of cells of mixed type. The cells can be mammalian cells. The cells can be human, mouse, rat, rabbit, goat, pig, or guinea pig cells. In some embodiments, the cells are human cells. In some embodiments, the cells are other types of animal, plant, fungal, bacterial, or protist cells. The cells can be any prokaryotic or eukaryotic cells.

In some embodiments, the cells are loaded onto the substrate at a concentration that reduces the probability of more than one cell being loaded into an individual microwell within the substrate. Loading of no more than one cell into individual microwells can be achieved by loading onto the substrate a cell suspension that contains fewer cells than the number of microwells in the substrate. In some preferred embodiments, the concentration of the cell suspension is adjusted so that the volume of the cell suspension used to load the substrate contains approximately one-tenth the number of cells as the number of microwells within the substrate. The cell suspension loaded onto the substrate can contain approximately one fourth, one fifth, one sixth, one seventh, one eighth, one ninth, or one tenth the number of microwells that are contained within the substrate. In some embodiments, loading comprises loading the cells such that no more than 20% of the cells are in microwells with other cells. In some embodiments, loading comprises loading the cells such that no more than 15% of the cells are in microwells with other cells. In some embodiments, loading comprises loading the cells such that no more than 10% of the cells are in microwells with other cells. In some embodiments, the loading comprises loading the cells such that no more than 5% of the cells are in microwells with other cells. In some embodiments, the loading comprises loading the cells such that no more than 1% of the cells are in microwells with other cells. The probability to find a given number of cells in a single microwell is typically governed by Poisson statistics.

In some embodiments, the invention provides methods of identifying the presence of an analyte. The analyte can be one or more biomolecules. The biomolecules can be oligonucleotide molecules, DNA molecules, RNA molecules, mRNA molecules, micro RNA molecules, tRNA molecules, and the like. In some embodiments, the biomolecules can be peptides or proteins. The biomolecules can be antibody heavy and light polypeptide chains, and/or receptor polypeptide chains (e.g., the alpha and beta chains of the T cell receptor). The analyte can be selected from the group consisting of antibodies, proteins, peptides, lipids, lipoproteins, amino acids, carbohydrates, oligonucleotides, viruses, exosomes, or a combination thereof.

Figure 9:
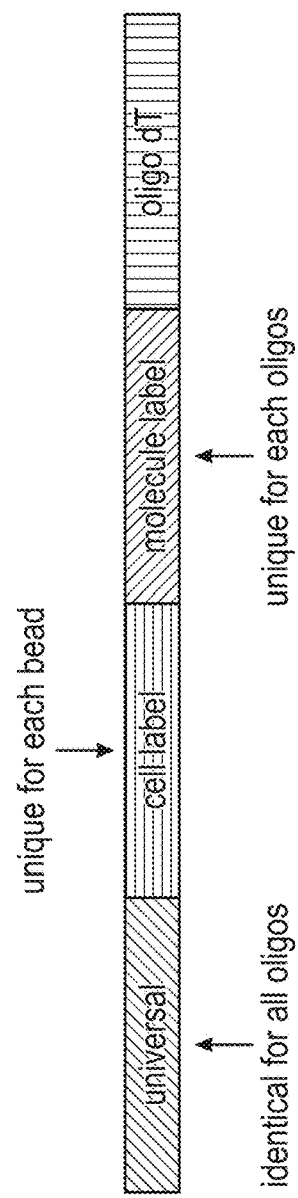
FIG. 9 shows the configuration of a non-limiting embodiment of a functionalized bead of the invention.
Figure 9:
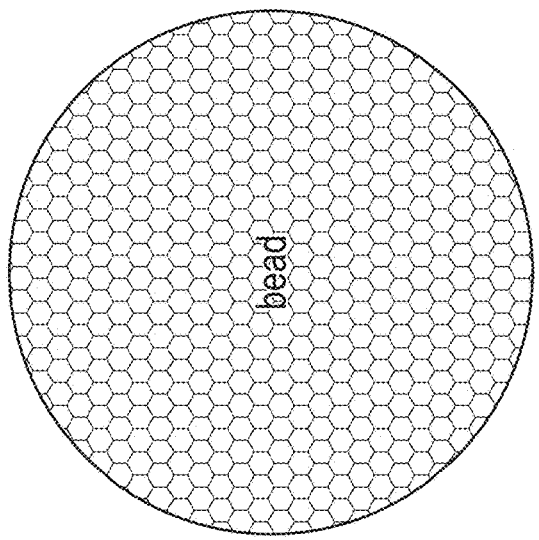
Figure 10:
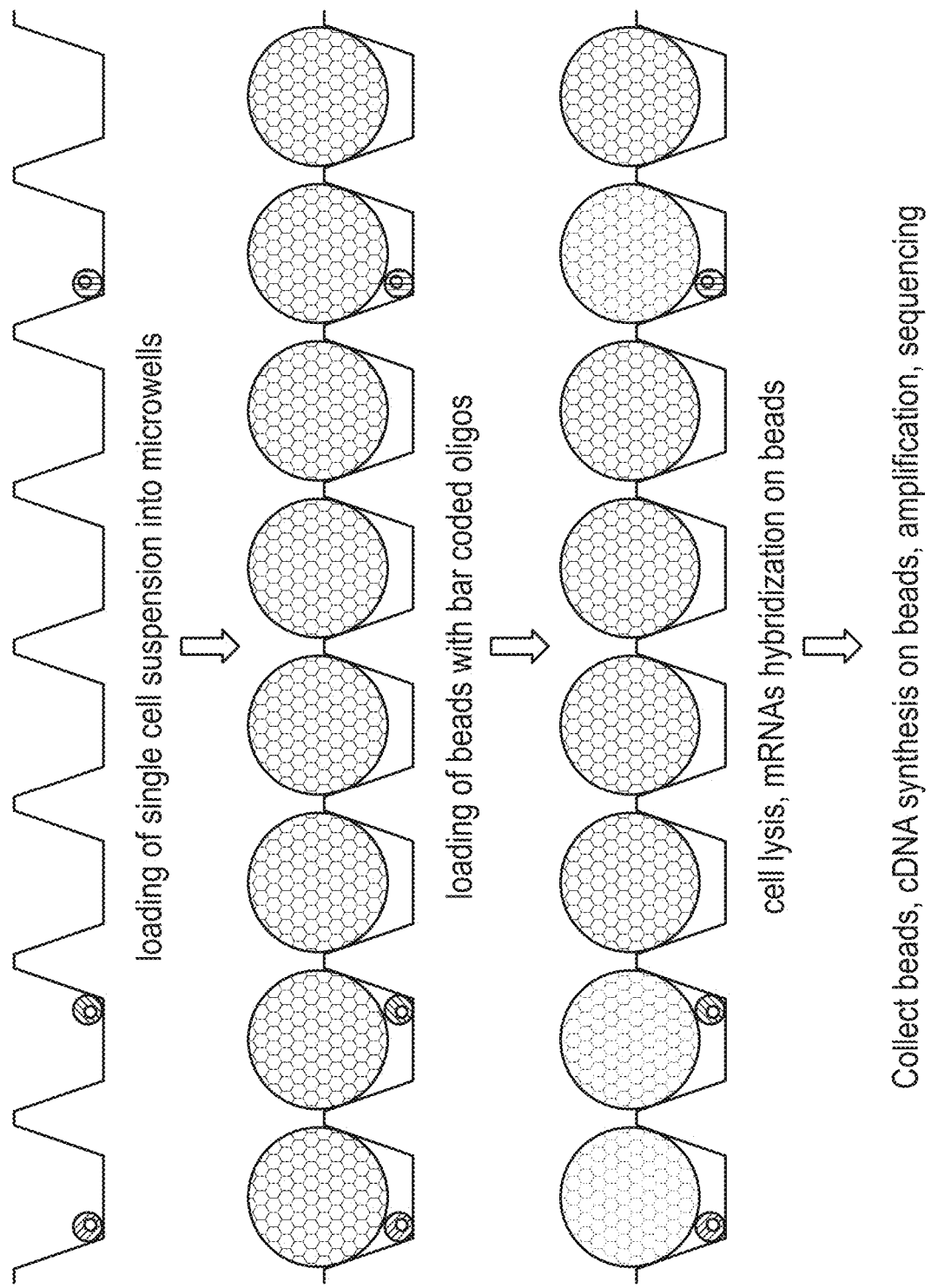
FIG. 10 shows a general process diagram for a non-limiting embodiment of a method for performing single cell expression analysis.

In at least some embodiments, the beads have one or more ligands for capturing (i.e. binding to) one or more analytes. The beads can have one or more copies of different ligands for capturing different target analytes. The ligands can be attached to the beads by covalent or non-covalent means. The ligands can be antibodies, proteins, peptides, oligonucleotides, or a combination thereof. The beads can comprise one or more nucleotides for conducting single cell expression analysis. Beads for single cell expression analysis can comprise (i) a cell identifying marker that is unique to each bead within a plurality of beads, and (ii) at least one ligand for binding a biomolecule of interest (i.e. analyte). Beads for single cell expression analysis can comprise a moiety wherein each moiety comprises (i) a cell identifying marker that is unique to each bead within a plurality of beads, (ii) a ligand for binding a biomolecule of interest (i.e. analyte), and (iii) a ligand index marker that is unique for each moiety. Beads for single cell expression analysis can comprise a plurality of capture ligands capable of hybridizing to a target nucleic acid, wherein each of the capture oligonucleotides comprises (i) an oligonucleotide cell marker that is unique to each bead, and (ii) an oligonucleotide label portion that is unique to each capture oligonucleotide. Suitable bead moieties for conducting single cell expression analysis according to the methods, system and kits of the invention include, but are not limited to, those disclosed in U.S. Patent Application Publication No. 2016/0289669, the entire contents of which are incorporated herein by reference for all purposes. One non-limiting embodiment of a bead for conducting single cell expression analysis is shown in FIG. 9.

In some embodiments, the analyte is secreted from a cell after the cell is enclosed in the analytical space between the bead and the bottom of the microwell. The cell can be incubated under conditions sufficient to permit the cell to secrete the analyte into the analytical space. The secreted analyte can be a biomolecule. The secreted analyte can be, for example, a cytokine, chemokine, mRNA, exosome, peptide, protein, glycoprotein, antibody, or amino acid. In some embodiments, the analyte can be released from the cells by cleavage (e.g. enzymatic cleavage). In some embodiments, cells within the sample are lysed after being enclosed between the beads and the bottom of the microwells and prior to conducting the analysis. Cell lysis may be implemented in assays wherein the analyte is an intracellular biomolecule. Cell lysis can be accomplished by chemical or biochemical means, by osmotic shock, or by means of thermal lysis, mechanical lysis, or optical lysis. In some embodiments, for example, cells may be lysed by addition of a cell lysis buffer comprising a detergent (e.g. SDS, Li dodecyl sulfate, Triton X-100, Tween-20, or NP-40), an organic solvent (e.g. methanol or acetone), or combinations thereof.

In some embodiments, the invention provides a method for determining the number of occurrences of a target nucleic acid in individual cells in a sample of cells. The method can be practiced by loading a sample of cells onto an array comprising a plurality of microwells, and loading a bead library onto the array. The geometry of the microwells and the beads in the library is paired such that the width of the beads is greater than the width of the bottom of the microwells. The geometry of the beads and microwells can be paired as specifically disclosed herein. Due to the geometric pairing of the beads and microwells, loading of the beads into the microwells results in the enclosure of individual cells within the microwells in small volumes in the space between the bottoms of individual beads and the bottoms of the microwells. The beads in the bead library can comprise a plurality of oligonucleotide ligands for capturing at least one target oligonucleotide. The oligonucleotide ligands can be conjugated to (i) an oligonucleotide cell marker that is unique to each bead, and (ii) an oligonucleotide label that is unique to each occurrence of the oligonucleotide ligand. One non-limiting embodiment for a bead comprising the oligonucleotide ligand is depicted in FIG. 9.

Once loaded into the microwell and enclosed in the space between the bottom of the bead and the bottom of the microwell, the individual cells can be incubated under conditions sufficient to permit the cells to secrete one or more target oligonucleotides. In some embodiments, the cells are lysed so as to release the target oligonucleotides into the small volume in the space between the bottom of the bead and the bottom of the microwell. With the target oligonucleotide in the space between the bottom of the bead and the bottom of the microwell, the target oligonucleotide is permitted to hybridize to the oligonucleotide ligand. The beads, with the target oligonucleotide hybridized to the oligonucleotide ligand, are collected. In some embodiments, the beads are magnetic and are collected using a magnet. In some embodiments, the beads are collected by dislodging the beads from the microwells through the use of a buffer solution that has higher density than the beads. Once the beads are collected, the hybridized target oligonucleotides are subjected to amplification to create a plurality of oligonucleotide conjugates that comprise (i) the hybridized target nucleic acid, (ii) an oligonucleotide that is complimentary to the oligonucleotide cell marker, and the (iii) the oligonucleotide label. The amplified oligonucleotide conjugates are then used to determine the number of occurrences of the target oligonucleotides that are expressed by individual cells within the cell sample. Methods for amplifying the oligonucleotide conjugates and correlating them with the number of occurrences of the target oligonucleotides expressed by individual cells are disclosed in the following references, the entire contents of which are incorporated herein by reference in their entirety for all purposes: U.S. Patent Application Publication No. 2016/0289669; Bose et al. Genome Biology (2015) 16:120; and Fan et al. Science (2015) Vol 347, Issue 6222, P. 1258367-1.

In at least one embodiment, the invention provides a method for loading a sample into a microwell. The method can be practiced by geometrically pairing a bead and microwell as disclosed herein, loading a sample into the microwell, and loading the bead into the microwell, wherein loading the bead into the microwell contacts the periphery of the bead with the walls of the microwell thereby anchoring the bead within the microwell and enclosing the sample within a space between bottom of the anchored bead and the bottom of the microwell. The sample can then be analyzed for the presence of one or more analytes, including determining the number of occurrences and/or concentration of the analytes. The sample can be assayed for its bioactivity. The bead can be contained within a plurality of beads that are loaded onto a substrate comprising a plurality of the microwells.

In at least one embodiment, the invention provides a kit for analyzing the bioactivity of a sample. The kit can be used for determining the presence and/or amount of one or more analytes in a sample. The kit can comprise a microwell and bead that are geometrically paired as disclosed herein such that loading the bead into the microwell contacts the periphery of the bead with the walls of the microwell thereby creating an enclosed space between the bottom of the microwell and the surface of the bottom part of the bead down from the interface formed between the periphery of the bead and the walls of the microwell. The kit can comprise a plurality of beads and a plurality of microwells within a substrate. The plurality of beads can be suspended within a liquid carrier. The beads can be conjugated to a ligand for binding an analyte (e.g. biomolecule) of interest as disclosed herein. The kit can comprise a plurality of beads and a separate liquid carrier for creating a suspension that comprises the plurality of beads. The beads can contain one or more ligands for capturing a targeted analyte as disclosed herein. The kit can contain one or more ligands and reagents for attaching the ligands to the beads. The kit and its individual components can be placed within a container, wrap (e.g. shrink wrap), bag or other suitable packaging, and can include instructions for analyzing the bioactivity of a sample, including detecting the presence and/or amount of one or more analytes contained within the sample.

Example 1—Microwell Analysis

An array of microwells with shapes of polygonal or conical frusta, with diameters of 10-50 μm at the bottom, 50-130 μm at the top, and 30-150 μm height is used. The microwells are filled with a medium and a suspension of cells is loaded onto the array. Cells are typically loaded in a ratio of 1:10 to the microwells, while an effort is made to distribute cells as evenly as possible over the area of the array. Cells are allowed sufficient time to sediment onto bottoms of the microwells. After that, a suspension of beads with a near-uniform diameter in a 10-100 μm range is loaded onto the microwell array, typically at a bead to microwell ratio of 1.1:1 to 1.5:1. Surfaces of the beads are functionalized, typically with oligonucleotides or antibodies, to bind molecules released by cells. Sufficient time is allowed for beads to settle into the microwells, and an effort is made to spread beads as uniformly as possible over the array, making sure that there is a bead in every microwell. The next step is different for different types of assays. If the goal is to capture cellular content, cells in the microwells are lysed and sufficient time is allowed for molecules released from cells to bind to beads. If the goal is to capture molecules secreted by live cells, sufficient incubation time is allowed to capture these molecules on the beads, with optional stimulation of cells during the incubation. Finally, the analysis of molecules captured on the beads is performed either inside or outside the microwell array.

Example 2—Demonstration of Microwell Sealing

Figure 11:
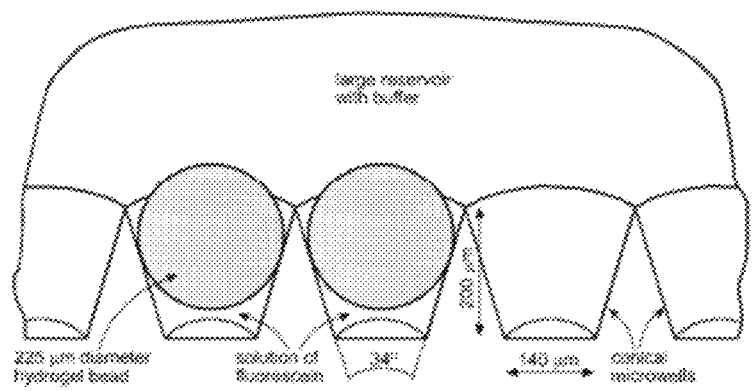
FIG. 11 shows a schematic of an embodiment of the inventive microwell used in connection with Example 2.
Figure 12:
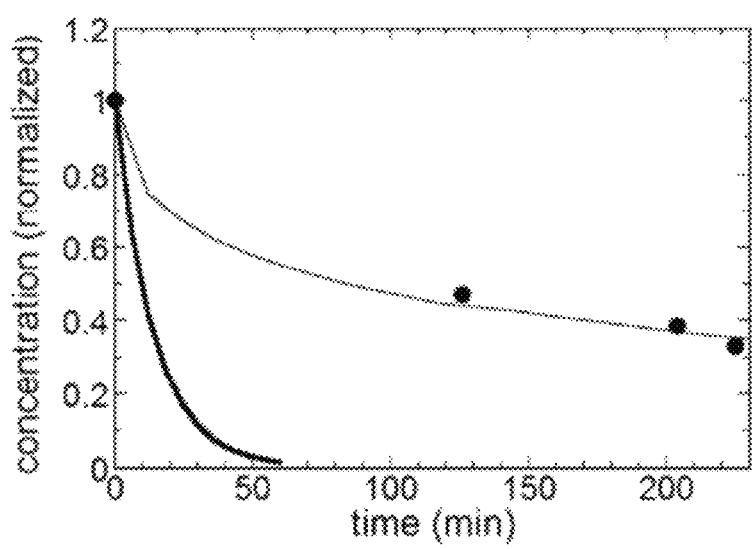
FIG. 12 is a graph showing the results for the experiments and numerical simulations obtained from Example 2, with different parameters plotted as a function of time: concentration of fluorescein, which is proportional to its fluorescence, normalized to the concentration in the beginning of the experiment (circles); concentration of fluorescein from a numerical simulation with a solid bead and 0.05 µm gap between the bead and conical sidewalls (thick curve); concentration of fluorescein from a numerical simulation with a porous bead and an effective coefficient of diffusion of 0.062 µm²/s inside the bead (thin curve).

The practicality of sealing the conical microwells with beads was tested in an experiment with an array of microwells with shapes of conical frusta with 140 μm diameters at the bottom, 200 μm depths, and 34° opening angles such as depicted in FIG. 11. The beads had diameters of 225 μm and were made of hydrogel. The microwells were filled with a solution of fluorescein (a small molecule fluorescent dye, with a molecular weight of 332 and a diffusion coefficient in water of 425 $\mu m^2/s$) to a depth of 5 mm. A suspension of the beads was loaded onto the microwells, and beads were allowed to sediment and fall into the microwells. The medium in the microwells was exchanged to plain buffer by repeated aspiration and dispensing of buffer. After several repetitions, there was no detectable fluorescence in microwells without beads, whereas in microwells with beads, medium under the beads remained strongly fluorescent, indicating the presence of fluorescein under the beads (see FIG. 12). Fluorescence of fluorescein under beads in two adjacent microwells was then measured under a fluorescence video-microscope as a function of time. Average levels of fluorescence from central areas of the two microwells (after the background fluorescence is subtracted) normalized to the average level in the beginning of the experiment were plotted at different time points (see FIG. 12). The results showed that the fluorescence under the beads decayed to 50% of its initial level after ~90 min, indicating that the elution of fluorescein from under the beads was slow and that the beads were sealing the microwells tightly.

To obtain a more quantitative estimate of the quality of sealing of the microwells by the beads, diffusion of fluorescein from under beads in microwells was numerically simulated in Comsol. In the case of a solid 225 μm diameter bead with a 0.05 μm gap between the bead and the conical sidewalls of a microwell with the shape and dimensions as in the experiment, the simulation predicted the concentration of fluorescein under the bead to decay to 50% after ~6 min (thick curve, FIG. 12), which was a 15-fold shorter time than the decay time observed in the experiment. Therefore, the sealing of the microwells observed in the experiment was much more efficient than it would be for a 0.05 μm gap between the beads and the sidewalls. On the other hand, the experimental data was consistent with predictions of the numerical simulations for the case, when the microwell is tightly sealed (zero gap) by a porous bead with an effective diffusion coefficient of fluorescein of 0.062 $\mu m^2/s$ inside the bead (thin curve, FIG. 12). This number is 7,000 lower than the coefficient of diffusion of fluorescein in water and is consistent with experimentally measured coefficient of diffusion of fluorescein in the hydrogel material of the beads. Therefore, the results of the numerical simulations confirmed that the hydrogel beads sealed the microwells tightly.

Example 3—Demonstration of Some Advantages of Conical Microwells and the Pairing of Microwell and Bead Geometry Configuring microwells in a conical shape can ensure that only one bead enters each microwell. In tests of conically shaped microwell arrays that involved >10,000 of monodisperse beads, it was never observed that more than one bead entered a microwell.

Additionally, when in a conical microwell, a bead rests on the conical sidewalls and is positioned at a well-defined, small distance above the microwell bottom. When the parameters of the microwells and diameter of the bead are properly chosen, the volume of medium between the bottom of the bead and the cell (or cells) on the microwell bottom can be reduced to a minimum, while avoiding the unwanted physical contact between the bead and the cell (cells). This feature makes microwells of the invention advantageous for assays involving hybridization of molecules released by cells or from lysed cells with molecules carried by beads. Because the hybridization occurs in a minimal volume with a proportionally high concentration of molecules released by cells (or from cells), an efficient and fast binding of target molecules to the beads can be achieved.

As a demonstration of this principle, microwells were made with 15 μm diameter at the bottom, ~60 μm depth, and 34° opening angles, and monodisperse 30 μm diameter beads were loaded onto the microwell array. The volume of medium between the bead and microwell bottom was <5 pL, while the bottom of the bead was >10 μm above the bottom of the microwell, providing substantial clearance between the bead and a cell at the microwell bottom. As a comparison, in the microwell arrays used for single-cell RNA-sequencing which are covered by a semipermeable membrane as taught by Gierahn et al. (Nat Methods. 2017 April; 14(4): 395-398), the volume of medium in the microwells (where hybridization is designed to occur) was ~50 pL which is 10-times greater and is expected to result in 10-fold lower concentration of molecules released by cells (or from cells) and a substantially slower and less efficient hybridization. Moreover, in droplet-based assays, a cell and a bead are typically confined in a droplet of medium with a volume of 1-2 nL, making the concentration of molecules released from the cell at least two orders of magnitudes lower than in the implementation of the microwell configuration of the invention.

All publications, patents, and patent applications mentioned in this specification are herein incorporated by reference to the same extent as if each individual publication, patent, or patent application was specifically and individually indicated to be incorporated by reference in its entirety. In the event of a conflict between a term herein and a term in an incorporated reference, the term herein controls.

The invention claimed is:
1. A kit for conducting an assay, comprising:
a) a substrate comprising a plurality of microwells, each of said microwells having an opening and a bottom, wherein said opening has a draft angle of at least 10 degrees; and
b) a plurality of beads, wherein said beads (i) each comprise a ligand adapted to capture a target analyte, (ii) are wider than said bottom of said microwells, and (iii) are adapted to seal said microwells, wherein said beads and said micro wells are geometrically paired such that only one bead in said plurality of beads can anchor within one microwell in said plurality of microwells;
wherein said substrate and said beads are adapted to permit (iv) the removal of said beads from said substrate after said beads have anchored within said microwells, and (v) the detection of binding of said ligand to said target analyte after said anchored beads have been removed from said microwells.

2. The kit of claim 1, wherein said opening of said microwells is wider than said bottom of said microwells.

3. The kit of claim 1, wherein said micro wells have a horizontal cross-sectional shape selected from the group consisting of circular, polygonal, and a combination thereof.

4. The kit of claim 1, wherein said microwells have a shape selected from the group consisting of a polyhedron, inverted cone, inverted pyramid, and combinations thereof.

5. The kit of claim 1, wherein said microwells are in the shape of a frustum.

6. The kit of claim 5, wherein said microwells have the shape of an inverted cone.

7. The kit of claim 1, wherein the width of said opening is between about 40 lam and about 130 μm.

8. The kit of claim 1, wherein the width of said bottom is between about 5 μm and about 30 μm.

9. The kit of claim 1, wherein said beads have a width that is between about 20 μm and about 100 μm.

10. The kit of claim 1, wherein said ligand is on a surface of said beads.

11. The kit of claim 1, wherein said ligand is selected from the group consisting of an antibody, protein, peptide, oligonucleotide, and combinations thereof.

12. The kit of claim 1, wherein each bead in said plurality of beads comprises a label that is unique to each bead in said plurality of beads.

13. The kit of claim 1, wherein each bead in said plurality of beads comprises at least one oligonucleotide comprising: (i) a ligand portion adapted to hybridize with a target oligonucleotide, wherein said ligand portion forms said ligand; (ii) a first label portion that is unique to each bead in said plurality of beads; and (iii) a second label portion that is unique to each oligonucleotide in said at least one oligonucleotide.

14. The kit of claim 1, wherein said microwells comprise an inner wall and the geometry of said beads and the geometry of said microwells is paired such that a periphery of said beads contacts said inner wall of said microwells when said beads are anchored within said microwells thereby creating a seal at the interface of said periphery of said beads and said inner wall of said micro wells.

15. The kit of claim 1, wherein said beads are magnetic.
16. A method for identifying the presence of an analyte in a sample, comprising:
a) providing a substrate comprising a plurality of micro wells each having (i) an opening with a draft angle of at least 10 degrees, and (ii) a bottom;
b) loading a sample into said microwells;
c) contacting said microwells with a plurality of beads each having a ligand capable of binding an analyte, wherein (i) said beads are wider than said bottom of said microwells and are adapted to seal said microwells, and (ii) contacting said microwells with said beads anchors said beads in said microwells thereby sealing said sample in said microwells;
d) incubating said sample under conditions sufficient for said ligand to bind said analyte; and
e) removing said anchored beads from said microwells;
f) detecting binding of said ligand to said analyte after said anchored beads are removed from said microwells thereby identifying the presence of said analyte in said sample;
wherein (i) said beads and said microwells are geometrically paired such that only one of said-beads in said plurality of beads can anchor within one microwell in said plurality of microwells when said micro wells are contacted with said beads; and (ii) said substrate and said beads are adapted to permit the removal of said beads from said substrate after said beads have anchored within said micro wells.

17. The method of claim 16, wherein said analyte is selected from the group consisting of an antibody, protein, peptide, lipid, lipoprotein, amino acid, carbohydrate, oligonucleotide, virus and combinations thereof.

18. The method of claim 16, wherein said analyte is DNA or RNA.

19. The method of claim 16, wherein said sample comprises a cell or a plurality of cells and detecting binding of said ligand to said analyte identifies a biomolecule that is (i) secreted by said cell or said plurality of cells, or (ii) is released by lysis of said cell or said plurality of cells.

20. The method of claim 16, wherein (i) loading said sample comprises loading single cells or a plurality of cells into said micro wells; and (ii) contacting said microwells with said beads encloses said single cells or said plurality of cells in said microwells.

21. The method of claim 20, wherein said analyte comprises at least one biomolecule.

22. The method of claim 21, wherein said beads comprise at least one ligand and said detecting: (i) comprises detecting the binding of said at least one ligand to said at least one biomolecule; and (ii) identifies (x) the secretion of said at least one biomolecule by said single cells or said plurality of cells, or (y) the release of said at least one biomolecule by lysis of said single cells or said plurality of cells.

23. The method of claim 21, wherein each bead in said plurality of beads comprises a plurality of different ligands and said detecting: (i) comprises detecting the binding of said ligands to a plurality of different biomolecules; and (ii) provides a profile of biomolecules (x) secreted by said single cells or said plurality of cells, or (y) released by lysis of said single cells or said plurality of cells.

24. The method of claim 16, wherein said microwells comprise an inner wall and the geometry of said beads and the geometry of said-microwells is paired such that a periphery of said beads contacts said inner wall of said microwells when said beads are anchored within said microwells thereby creating a seal at the interface of said periphery of said beads and said inner wall of said microwells.

25. The kit of claim 14, wherein said beads have a radius and said microwells and said beads are geometrically paired such that a portion of said beads protrudes above said opening at a height that is equal to or less than said radius when said beads are anchored within said microwells and said periphery of said beads is in contact with said inner wall.

26. The method of claim 24, wherein said beads have a radius and said microwells and said beads are geometrically paired such that a portion of said beads protrudes above said opening at a height that is equal to or less than said radius when said beads are anchored within said microwells and said periphery of said beads is in contact with said inner wall.

27. The method of claim 16, wherein said ligand is on the surface of said beads.

* * * * *